United States Patent [19]

Ying

[11] Patent Number: 4,540,723
[45] Date of Patent: Sep. 10, 1985

[54] DENTAL RESTORATIVE COMPOSITION CONTAINING MONOFUNCTIONAL MONOMER AND DIOLEFINICALLY UNSATURATED MONOMER

[75] Inventor: Lincoln Ying, Bridgewater, N.J.

[73] Assignee: J&J Dental Products Inc., East Windsor, N.J.

[21] Appl. No.: 610,909

[22] Filed: May 16, 1984

[51] Int. Cl.$^3$ ............................................. C08L 33/08
[52] U.S. Cl. ................................... 523/115; 523/109; 523/116; 204/159.22
[58] Field of Search ....................... 523/115, 109, 116

[56] References Cited

U.S. PATENT DOCUMENTS 4,426,504 1/1984 Nandi .................................. 523/115
4,433,958 2/1984 Fellman et al. ...................... 523/115

Primary Examiner—Harold D. Anderson
Attorney, Agent, or Firm—Charles J. Metz

[57] ABSTRACT

A dental restorative composition containing a monofunctional aromatic or cycloaliphatic acrylate or methacrylate, such as benzyl methacrylate.

6 Claims, No Drawings

DENTAL RESTORATIVE COMPOSITION CONTAINING MONOFUNCTIONAL MONOMER AND DIOLEFINICALLY UNSATURATED MONOMER

The invention relates to a dental restorative composition containing a monofunctional aromatic or cycloaliphatic acrylate or methacrylate monomer.

BACKGROUND OF THE INVENTION

In U.S. patent application Ser. No. 509,770, filed July 1, 1983, now U.S. Pat. No. 4,500,657, for DENTAL RESTORATIVE COMPOSITIONS HAVING IMPROVED MECHANICAL PROPERTIES AND HYDROLYTIC STABILITY, and assigned to the same assignee as this Application, there is disclosed dental restorative compositions containing a monomer having at least two olefinically unsaturated groups, a polymerization initiator, and a filler. In the invention of said Application, both the monomer and the filler are hydrophobic (as defined therein), and the filler has a critical particle size and constitutes a critical proportion of the formulation. The dental restorative compositions of said application exhibit excellent properties, and are serious contenders to be indicated for use in Class II restorations (that is, restorations on the biting surfaces of molars), a distinction that has, thus far, eluded most, if not all, commercial resinous dental restoratives.

This invention is directed to an improvement in the art of resinous dental restoratives, and is particularly useful in the restoratives described in said Application.

BRIEF DESCRIPTION OF THE INVENTION

The invention provides a dental restorative composition comprising a polymerizable composition containing at least two olefinically unsaturated groups, a polymerization initiator for said composition, a filler, and a minor proportion of a monofunctional aromatic or cycloaliphatic acrylate or methacrylate. Preferred monofunctional monomers include benzyl methacrylate and 3,3,5-trimethylcyclohexyl methacrylate.

THE PRIOR ART

McNall, in U.S. Pat. No. 3,955,282, and Lee et al., in U.S. Pat. No. 4,340,529, disclose the use of benzyl methacrylate as one possible component in an orthodontic bracket cement.

O'Sullivan et al., in U.S. Pat. Nos. 3,931,678 and 4,243,578, disclose the use of cyclohexyl methacrylate as a "solvent" in a urethane polymer-based dental filling composition.

Lee et al., in U.S. Pat. No. 4,340,532, disclose the use of cyclohexyl methacrylate as one possible monomeric component in a dental adhesive composition.

DETAILED DESCRIPTION OF THE INVENTION

The composition of the invention contains at least one polymerizable composition having at least two olefinically unsaturated groups. Such materials are well known in the art and need to be illustrated by only a few examples. It is preferred that the olefinically unsaturated compound be an acrylic or methacrylic ester, and particularly, a compound having two or more acrylic or methacrylic ester groups because of the polyfunctional acrylic esters exhibit less shrinkage upon polymerization than do the monofunctional acrylic esters and also provide cross-linking. Specific types of acrylic esters that are useful include: alkane diol acrylates or methacrylates such as the $C_4$-$C_{12}$ alkane diol acrylates or methacrylates, e.g., 1,10-decamethylene diol dimethacrylate and 1,6-hexamethylene diol dimethacrylate; the polyalkylene glycol acrylates or methacrylates, such as triethylene glycol dimethacrylate and tetraethylene glycol dimethacrylate; bisphenol-A acrylate or methacrylate esters; alkoxylated bisphenol-A acrylate or methacrylate esters, e.g., ethoxylated bisphenol-A dimethylacrylate; bisphenol-A diglycidyl dimethylacrylate ("bis-GMA") and the like. Other multifunctional acrylic or methacrylic esters that can be used include methacrylate-terminated polyurethanes, trimethylolpropane trimethyacrylate or triacrylate, and the like.

The dental restorative composition of the invention includes a polymerization initiator. Such initiators are known in the art and can be used in their customary proportions. For instance, the composition can be divided, one package containing a peroxide such as benzoyl peroxide, and the other containing an activator for the peroxide such as N,N-di-(2-hydroxyethyl)-p-toluidene. Other initiator systems known in the art can also be used.

In order to minimize the formation of voids, in a preferred aspect of the invention, the initiator is a photosensitive initiator system so that the just-prior-to-use mixing step necessary for the two-component, self-curing composite systems can be avoided. In this aspect, a one-package system is used. Resin, filler, and the photosensitive initiator system are mixed under a vacuum to reduce void formation. The composition then needs no further mixing by the dentist or dental technician. Such photosensitive initiator systems include benzoin, benzoin ethers and esters, 2,2-diethoxy acetophenone, and the diketone compounds plus a tertiary amine reducing agent, such as those that are disclosed by Dart et al., U.S. Pat. No. 4,071,424. Specific examples of preferred photoinitiator systems include benzil and/or camphoroquinone plus N,N-dimethylaminoethyl methacrylate or ethyl 4-(N,N-dimethylamino)benzoate.

The composition of the invention contains fillers such as silica, powdered glass, powdered quartz, or the like, which are conventional in the art.

Preferably, the filler employed in the invention has a volume average particle size below 15 microns, and preferably, below 5 microns. Thirty percent of the filler particles, and preferably 70 to 100 percent, have a size below 5 microns. The filler is preferably employed in an amount within the range of from about 35 to about 78 volume percent, based on the volume of the filler plus the polymerizable composition. Thus, the filler is preferably employed in relatively high proportions. A volume percent of 35 to 78 corresponds approximately to 50 to 95 weight percent of the dental restorative composition of the invention, depending on the specific gravity of the filler.

It is also preferable to use hydrophobic, chemically durable fillers such as quartz and/or a particular heat-treated barium or strontium glass. Such hydophobic fillers will absorb less than 0.1 weight percent water (prior to addition of silane coupling agent) when exposed to normal ambient conditions. Water content of the filler is determined by a differential scanning calorimeter ("DSC"). The first departure from baseline in a DSC scan is caused by the presence of water. To determine the amount present, the area under the peak is determined and normalized relative to the weight of the sample.

The barium or strontium glass that may be employed as the filler is selected for chemical durability, as is evidenced by resistance to leaching in an aqueous environment. Such glasses are substantially free of alkali metal oxides, and are single phase glasses. If the mole percent of barium or strontium oxide exceeds a certain point, the glass becomes two-phased. This proportion can vary, depending upon the presence and proportion of other metal oxides in the glass. For one preferred type of glass that is composed of oxides of barium, silicon, boron, and aluminum, the upper limit for a single phase glass is about 20 mole percent barium oxide. One preferred glass for use in the invention has the following composition:

$SiO_2$—67 mole percent
$BaO$—16.4 mole percent
$B_2O_3$—10 mole percent
$Al_2O_3$—6.6 mole percent The essential ingredients in the glass are the oxides of barium and/or strontium and silicon. Oxides of other metals such as aluminum and boron may also be present so long as such oxides do not detract from the chemical durability of the glass. Thus, significant quantities of alkali metal oxides should be avoided because, as is well known, alkali metal ions are quite soluble in aqueous media, and therefore will reduce the chemical durability of the glass. The minimum barium and/or strontium content of the glass is preferably that which is sufficient to impart X-ray opacity to the glass.

The preferred barium and/or strontium glass powder is acid washed and then subjected to a heat treatment to enhance its resistance to attack by water. The procedures are the following:

The acid-washing treatment to which the glass powder is subjected is carried out by known procedures. For instance, a mixture of 1 part (by weight) of glass powder, 1 part of 37 percent aqueous hydrochloric acid, and 1 part of de-ionized water is stirred at room temperature for 45 minutes, filtered, and rinsed with de-ionized water until the pH of the filtrate is the same as the rinse water. The powder is then dried at about 50° C. overnight in a forced air oven. The acid wash is used to remove metal impurities from the glass and to reduce the amount of leachable barium or strontium from the surface of the glass.

The acid-washed glass powder is subjected to a heat treatment to reduce the affinity of the glass powder for water. This heat treatment is carried out at an elevated temperature below the sintering temperature of the glass powder (the sintering temperature can be determined by known procedures, as by thermo-mechanical analysis "TMA"), but high enough to cause a significant reduction in the specific surface area of the glass powder, as measured by known procedures such as by a "Quantasorb" B.E.T. surface area analyzer. The reduction in specific surface area will usually be at least 50 percent (i.e., the surface area of the heat treated glass powder will be less than about one-half that of the untreated powder), up to 80 to 90 percent, or even more in some cases. The heat treatment time is not at all critical in that it need be carried out only for the minimum time needed to heat all the powder to the desired temperature. Apparently the effect of the heat on the glass powder is quite rapid, and all that is required is to bring all of the mass of powder up to the desired temperature. However, since the glass powder is an excellent heat insulator, this can take several hours for masses of powder wherein the heat must travel through a significant thickness of powder to heat all of the glass to the desired temperature.

As is known in the art, a silane coupling agent can be employed to enhance the bond between the filler and the resin. Such coupling agents include gamma-methacryloxypropyltrimethoxysilane.

It is desirable to include a small percentage of colloidal silica in the composition in order to adjust the viscosity and the handling characteristics of the composite paste. For instance, from about 2 to about 25 weight percent of colloidal silica, based on weight of the entire composite, is beneficial.

The colloidal silica is preferably treated with a silane coupling agent such as gamma-methacryloxypropyltrimethoxysilicone ("A-174"). After such treatment, the silica should be protected from ambient moisture because it may absorb up to about 1 weight percent of water from the atmosphere, as measured by DSC.

The major novelty in this invention is the inclusion in the dental restorative formulation of a minor amount of a monofunctional aromatic or cycloaliphatic acrylate or methacrylate monomer such as benzyl methacrylate or 3,3,5-trimethylcyclohexyl methacrylate. (By "monofunctional" is meant that the monomer contains only one acrylate or methacrylate group.) The presence of the monofunctional monomer serves to increase the degree of cure of the resinous system, with accompanying improvement in several properties such as creep resistance, water absorption, and chemical resistance. A small but significant improvement in strength properties is also observed.

The monofunctional monomers used in the invention have the following characteristics: The monofunctional monomer acts as a chain extending or bridging agent to give a more complete cure to the polymerizing dental restorative formulation. The selected monomers preferably have boiling points at atmospheric pressure of above 50° C., so that the monomer will not bubble or boil alway during vacuum mixing of the ingredients of the composition. The aromatic or cycloaliphatic group enhances chemical resistance, compared with, for instance, a long chain alkyl methacrylate. Also, the monofunctional monomer has relatively low viscosity, which encourages wet-out of filler and serves to enable a more complete cure to take place. The monofunctional monomers that are used are mono-esters of acrylic or methacrylic acid wherein the alcohol moiety of the ester contains a cycloaliphatic or an aromatic group, and wherein any alkyl or alkylene groups that might be present are not more than about two or three carbon atoms long, in order to preserve the excellent chemical resistance inherent in aromatic or cycloaliphatic groups.

The preferred monofunctional monomers are benzyl methacrylate and 3,3,5-trimethylcyclohexyl methacrylate.

The monofunctional monomer is used in a minor proportion (i.e., less than one-half, by weight) of the monomer portion of the formulation, although the exact amount has not been found to be narrowly critical. Usually, the monofunctional monomer will be used in amounts of from about 5 to about 40 weight percent, based on the total monomer portion of the formulation.

The examples set forth below illustrate the invention.

The following materials were used in the Examples:
Ethoxylated bisphenol-A dimethacrylate ("EBDM")

Triethylene glycol dimethacrylate ("TEGDM")
1,6-hexamethylene glycol dimethacrylate ("HXDDM")
2,2'-propane bis[3-(4-phenoxy)-2-hydroxypropyl-1 methacrylate] ("Bis-GMA")
Benzyl methacrylate ("BMA")

In the examples and Control Examples, the ingredients were mixed, de-gassed to insure bubble-free cured compositions, and cured by exposure to a commercial light source for photoinitiated reactions. For the samples without filler, the ingredients were simply mixed and de-gassed in a vacuum oven at room temperature for about 30 minutes, and were then exposed to a FOTOFIL commercial light source for 60 seconds. The distance between the source and the sample was about 4 to 5 inches. For the samples that contained filler, the ingredients were mixed at about 50° C. in a Ross vacuum process mixer, and were cured by exposure to a FOTOFIL commercial light source for 60 seconds, with the sample being held 4 to 5 inches away from the source. The photoinitiator system used was a mixture of camphoroquinone, benzil, and ethyl 4-(N,N-dimethylamino)benzoate, in amounts of about 0.3%, 0.12%, and 1.2%, by weight, respectively, based on total monomer weight.

EXAMPLES 1–4 AND CONTROLS 1–6

Several neat (i.e., without filler) resin mixtures were cured as described above, and then tested for flexural strength, flexural modulus, creep resistance, and water sorption. The results are displayed below in Table I and Table II:

TABLE I

|  | Formulation | Flexural Strength* (MPa) | Flexural Modulus (MPa) |
|---|---|---|---|
| Control 1 | 70:30 Bis-GMA/TEGDM | 70 ± 17 | 2668 ± 177 |
| Control 2 | EBDM | 124 ± 8 | 2798 ± 49 |
| Control 3 | 90:10 EBDM/HXDDM | 117 ± 13 | 2772 ± 62 |
| Control 4 | 85:15 EBDM/HXDDM | 124 ± 9 | 2701 ± 73 |
| Control 5 | 80:20 EBDM/HXDDM | 127 ± 9 | 2670 ± 206 |
| Control 6 | 70:30 EBDM/HXDDM | 116 ± 5 | 2461 ± 46 |
| Example 1 | 90:5:5 EBDM/HSDDM/BMA | 127 ± 13 | 2879 ± 107 |
| Example 2 | 85:5:10 EBDM/HXDDM/BMA | 130 ± 11 | 2842 ± 171 |
| Example 3 | 80:5:15 EBDM/HXDDM/BMA | 122 ± 8 | 2967 ± 145 |
| Example 4 | 90:10 EBDM/BMA | 131 ± 11 | 3062 ± 117 |

*Samples aged in 37° C. water for 24 hours.

TABLE II

|  | Formulation | Creep* (%) | Water Sorption, % |
|---|---|---|---|
| Control 2 | EBDM | 1.79 ± 0.45 | 0.43 |
| Control 3 | 90:10 EBDM/HXDDM | 1.15 ± 0.22 | 0.47 |
| Control 4 | 85:15 EBDM/HXDDM | 1.27 ± 0.21 | 0.45 |
| Control 5 | 80:20 EBDM/HXDDM | 0.70 ± 0.02 | 0.49 |
| Control 6 | 70:30 EBDM/HXDDM | 0.98 ± 0.08 | 0.52 |
| Example 1 | 90:5:5 EBDM/HXDDM/BMA | 0.58 ± 0.22 | 0.45 |
| Example 2 | 85:5:10 EBDM/HXDDM/BMA | 0.63 ± 0.44 | 0.44 |
| Example 3 | 80:5:15 EBDM/HXDDM/BMA | 0.25 ± 0.24 | 0.12 |
| Example 4 | 90:10 EBDM/BMA | 0.24 ± 0.33 | 0.38 |

*Samples aged in 37° C. water for 24 hours.

EXAMPLE 5

A typical light-cured dental restorative composition was prepared, having the formulation listed in Table III. Representative physical properties are displayed in Table IV:

TABLE III

| Component | Formulation, Parts by Weight |
|---|---|
| Heat treated Ba Glass Filler[1] (avg. 3 micron) | 71 |
| Aerosil OX-50 Colloidal Silica[2] | 15 |
| Irganox 1010 | 0.0015 |
| EBDM | 10.9 |
| HXDDM | 0.68 |
| Benzyl methacrylate | 2.05 |
| Camphoroquinone | 0.038 |
| Benzil | 0.016 |
| Ethyl 4-(N,N—dimethylamino)benzoate | 0.164 |
| Cyasorb UV-9 | 0.136 |
| Ionol (BHT) | 0.0014 |

[1] Contained 1.5 weight percent A-174 silane.
[2] Contained 5 weight percent A-174 silane.

TABLE IV

| Physical Properties | |
|---|---|
|  | Example 5 (N/mm2) |
| Compression Strength | 377 |
| Diametral Tensile Strength | 67 |
| Flexural Strength | 132 |
| Flexural Modulus | 19700 |
| Rockwell Hardness (F scale) | 105 |
| Thermal Expansion | 28 ppm (25-90° C.) |

EXAMPLE 6 AND CONTROL EXAMPLE 7

Two dental restorative formulations were prepared, having the compositions set forth in Table V:

TABLE V

| Ingredient | Example 6 | Control 7 |
|---|---|---|
| Bis-GMA | — | 10.47 |
| TEGDM | — | 4.49 |
| EBDM | 10.9 | — |
| HXDDM | 0.68 | — |
| Benzyl Methacrylate | 2.05 | — |
| Camphoroquinone | 0.038 | 0.04 |
| Benzil | 0.016 | 0.02 |
| Ethyl 4-(N,N—dimethylamino)benzoate | 0.164 | 0.18 |
| Heat Treated Ba glass (avg. 3 microns; contained 1.5 wt % A-174) | 71 | 69.84 |
| OX-50 Colloidal Silica (contained 5 wt % A-174) | 15 | 14.96 |

The two materials were cured as described above, and were tested for creep modulus, water sorption, and depth of cure, with the results displayed in Table VI:

TABLE VI

| Creep Modulus, psi | Example 6 | Control 7 |
|---|---|---|
| Initial | $2.28 \times 10^6$ | $2.84 \times 10^6$ |
| 24 Hours | $2.11 \times 10^6$ | $2.05 \times 10^6$ |
| 96 Hours | $1.9 \times 10^6$ | $1.6 \times 10^6$ |
| Water Sorption, % | 0.27 | 1.0 |
| Depth of Cure | 4 mm | 2 mm |

The increased depth of cure and the lower percentage of loss in creep modulus is felt to be principally caused by the use of the monofunctional monomer in Example 6, compared with Control 7, which lacks the monofunctional monomer. The lower water sorption of Example 6 compared with Control 7 is caused, at least in part, to the use of EBDM rather than Bis-GMA, since the former is more hydrophobic. It is probable, however, that the improved degree of cure exhibited by the formulations containing the monofunctional monomer, also helps to reduce the water sorption, as is evidenced by the data reported in Table II.

The test procedures that were used to evaluate the Examples and Control Examples herein were the following:

Diametral tensile strength—ADA Specification No. 27, Paragraph 4.3.7, JADA 94, 1191 (1977).

Flexural Strength and Modulus—Three-point bend test. A molded beam, 1/16 inch in thickness, is supported across a gap of one inch and a stressing force is applied to the center of the beam midway between the supports, until the beam breaks. The speed of the Instron testing machine used is 0.05 cm/min.

Compression strength—A right cylinder of the polymerized dental restorative, after conditioning in a 37° C. water bath for 24 hours, is stressed in the compression mode by an Instron tester (at a speed of 0.05 cm/in), parallel to its long axis, until failure occurs.

Hardness—Rockwell F scale used

Thermal expansion—Thermo-mechanical analysis; ADA specified ranges of 25° to 90° C., @ 5° C./minute.

Depth of Cure—Samples of varying thicknesses are cured by a 20 second exposure to a Translux commercial light source. The top (i.e., the surface exposed to the light) and bottom hardnesses are determined, using Rockwell F scale, immediately after cure. The thickness of sample that yields a bottom surface hardness at least 65% of the top surface hardness is recorded as the depth of cure.

Water sorption—The procedure of ADA Specification No. 27, Paragraph 4.3.8, Jada 94, 1191 (1977), is modified in that samples $33 \times 7 \times 1.5$ millimeters are used, and the results are reported as % weight gain, instead of $mg/cm^2$.

Creep—ADA Specification No. 1, JADA 95, 614 (1977). The results are reported as percent of length change between 1 and 4 hours.

Creep Modulus—The creep test is carried out as above, with the results being reported as the load divided by the change in dimension.

What is claimed is:

1. A dental restorative composition comprising a polymerizable composition containing at least two olefinically unsaturated groups, a filler, and a minor proportion of a monofunctional monomer consisting essentially of benzyl acrylate or methacrylate.

2. The composition of claim 1 wherein the monofunctional monomer is benzyl methacrylate.

3. The dental restorative composition of claim 1 wherein the polymerizable composition is a methacrylic ester.

4. The dental restorative composition of claim 2 wherein the polymerizable composition is a methacrylic ester.

5. The dental restorative composition of claim 3 wherein the methacrylic ester comprises ethoxylated bisphenol-A dimethacrylate.

6. The dental restorative composition of claim 4 wherein the methacrylic ester comprises ethoxylated bisphenol-A dimethacrylate.

* * * * *